United States Patent
Shimizu et al.

(10) Patent No.: US 11,458,688 B2
(45) Date of Patent: Oct. 4, 2022

(54) TUBULAR TISSUE PREPARATION DEVICE, TUBULAR TISSUE PREPARATION KIT, AND TUBULAR TISSUE PREPARATION METHOD

(71) Applicant: TOKYO WOMEN'S MEDICAL UNIVERSITY, Tokyo (JP)

(72) Inventors: Shogo Shimizu, Tokyo (JP); Kazunori Sano, Fujinomiya (JP); Hidekazu Sekine, Tokyo (JP); Tatsuya Shimizu, Tokyo (JP)

(73) Assignee: Tokyo Women's Medical University, Tokyo (JP)

( * ) Notice: Subject to any disclaimer, the term of this patent is extended or adjusted under 35 U.S.C. 154(b) by 345 days.

(21) Appl. No.: 16/771,203

(22) PCT Filed: Oct. 19, 2018

(86) PCT No.: PCT/JP2018/039072
§ 371 (c)(1),
(2) Date: Jun. 9, 2020

(87) PCT Pub. No.: WO2019/116726
PCT Pub. Date: Jun. 20, 2019

(65) Prior Publication Data
US 2020/0368972 A1 Nov. 26, 2020

(30) Foreign Application Priority Data
Dec. 11, 2017 (JP) .............................. JP2017-236746

(51) Int. Cl.
*B33Y 30/00* (2015.01)
*B33Y 50/02* (2015.01)
(Continued)

(52) U.S. Cl.
CPC ............ *B29C 64/393* (2017.08); *B33Y 30/00* (2014.12); *B33Y 50/02* (2014.12); *B33Y 70/00* (2014.12);
(Continued)

(58) Field of Classification Search
CPC ....... A61L 27/38; A61L 27/50; B29C 64/393; B33Y 30/00; B33Y 50/02; B33Y 70/00;
(Continued)

(56) References Cited

U.S. PATENT DOCUMENTS 4,839,280 A * 6/1989 Banes .................... C08J 7/14
428/447
5,284,766 A 2/1994 Okano et al.
(Continued)

FOREIGN PATENT DOCUMENTS

EP 1891914 A1 * 2/2008 ............... A61F 2/84
JP H02-211865 A 8/1990
(Continued)

OTHER PUBLICATIONS

Sekine, et al.; Pulsatile Myocardial Tubes Fabricated With Cell Sheet Engineering; Circulation; Jul. 4, 2006; 114[suppl I]:I-87-I-93.
(Continued)

*Primary Examiner* — Anh T Vo
(74) *Attorney, Agent, or Firm* — Kilpatrick Townsend & Stockton LLP (57) ABSTRACT

The present invention provides a tubular tissue preparation device provided with: a chamber for accommodating a tubular support body; a first support part for communicating the inside and the outside of the chamber and fixing the tubular support body; and a pressurizing/depressurizing means for controlling the pressure in an inner space of the chamber, wherein the first support part is for fixing a first opening section of the tubular support body, communicating
(Continued)

a lumen of the tubular support body and the outside of the chamber, and separating the lumen of the tubular support body and the inner space of the chamber. Also, the present invention provides a tubular tissue preparation kit that includes said device and a device for transporting sheet-shaped tissue. In addition, the present invention provides a tubular tissue preparation method using said device.

15 Claims, 9 Drawing Sheets

(51) Int. Cl.
  *B33Y 70/00* (2020.01)
  *B33Y 80/00* (2015.01)
  *B29C 64/393* (2017.01)
  *C12M 3/00* (2006.01)
  *C12M 1/34* (2006.01)

(52) U.S. Cl.
  CPC ............ *B33Y 80/00* (2014.12); *C12M 21/08* (2013.01); *C12M 41/40* (2013.01)

(58) Field of Classification Search
  CPC ......... B33Y 80/00; C12M 1/00; C12M 21/08; C12M 25/14; C12M 41/40
  See application file for complete search history.

(56) References Cited

U.S. PATENT DOCUMENTS

| | | | |
|---|---|---|---|
| 6,107,081 A * | 8/2000 | Feeback | G01N 3/08 435/284.1 |
| 2013/0171213 A1 | 7/2013 | Sekine et al. | |
| 2014/0255967 A1 | 9/2014 | Dancu | |
| 2020/0352550 A1 | 11/2020 | Maeda et al. | |

FOREIGN PATENT DOCUMENTS

| | | |
|---|---|---|
| JP | 2005-502351 A | 1/2005 |
| JP | 2008-079783 A | 4/2008 |
| JP | 2008-148887 A | 7/2008 |
| JP | 2010-539938 A | 12/2010 |
| WO | WO 2003/22985 A2 | 3/2003 |
| WO | WO 2003/089566 A1 | 10/2003 |
| WO | WO 2007/009036 A2 | 1/2007 |
| WO | WO 2009/042639 A2 | 4/2009 |
| WO | WO 2012/036224 A | 3/2012 |
| WO | WO 2017/043600 A1 | 3/2017 |

OTHER PUBLICATIONS

Japan Patent Office; International Search Report, dated Dec. 18, 2018; PCT/JP2018/039072.
European Patent Office; Supplementary European Search Report of EP 18887289, completed Jun. 22, 2021.

* cited by examiner

FIG. 8

TUBULAR TISSUE PREPARATION DEVICE, TUBULAR TISSUE PREPARATION KIT, AND TUBULAR TISSUE PREPARATION METHOD

CROSS REFERENCE TO RELATED APPLICATIONS

This application is a National Phase entry of International Application No. PCT/JP2018/039072, filed Oct. 19, 2018, which claims priority to Japanese Patent Application No. 2017-236746, filed Dec. 11, 2017, the disclosures of which are hereby incorporated by reference in their entireties for all purposes.

FIELD

The present invention relates to a tubular tissue preparation device, a tubular tissue preparation kit, and a tubular tissue preparation method. Note that this application claims priority based on Japanese Patent Application No. 2017-236746 filed on 11 Dec. 2017 to the Japan Patent Office and the entire specification is incorporated herein by reference.

BACKGROUND

In recent years, techniques for fabricating three-dimensional tissue and organs using cells for the purpose of regenerative medicine or drug response tissue models have been developed. Conventionally, the majority of adherent cells could only be cultured two-dimensionally (planar) in vitro. However, the majority of tissues in the body are constructed by three-dimensionally layering cells, and so in order to get close to the conditions within the body a technique for three-dimensional construction of cells is required.

Attempts to produce three-dimensional constructs of cells include, for example, the development of methods such as: three-dimensionally constructing tissue by inoculating cells onto a so-called scaffold and then transplanting the same; decellularizing organs or tissue, using the remaining matrix as a scaffold, and inoculating the scaffold with cells which form a three-dimensional construct; and three-dimensionally layering cell sheets that have separated in sheet form so as to construct tissue. All of these techniques are expected to be applied to the fields of regenerative medicine and drug discovery and early implementation thereof is highly anticipated.

In order to fabricate cell sheets, a cell culture dish with a culture substrate surface covered by a polymer having an upper or lower critical solution temperature with respect to water of 0 to 80° C. (temperature-responsive culture dish) has been developed (PTL 1). Cells are cultured using this cell culture dish below the upper critical solution temperature or at or above the lower critical solution temperature of the polymer covering the surface of the cell culture dish, and once the cells have been cultured to confluence the cells can be recovered noninvasively as a cell sheet by bringing the temperature to at or below the upper critical solution temperature or below the lower critical solution temperature.

The establishment of methods for fabricating cell sheets has dramatically changed cell therapy techniques. However, for critically ill patients for whom cell transplantation does not exhibit therapeutic effects, organ transplantation remains an effective therapeutic means. With respect to the number of patients who require organ transplantation, the number of organs that can be provided is exceedingly small and so the development of a technique for constructing organs or tissue in vitro is desired. Cell sheet engineering techniques have been applied to such problems and the construction of thick three-dimensional biological tissue have been attempted by layering cell sheets. For example, a method for fabricating tissue with a vascular network has been developed by stepwisely layering cell sheets on a vascular bed (PTL 2). Furthermore, not only have there been attempts to fabricate planar tissue but attempts have also been made to add a pump function by wrapping a cardiomyocyte sheet onto tubular blood vessels (NPL 1).

CITATION LIST

Patent Literature

[PTL 1] Japanese Unexamined Patent Publication (Kokai) No. 02-211865
[PTL 2] WO2012/036224

Non-Patent Literature

[NPL 1] Sekine H, et al., Pulsatile myocardial tubes fabricated with cell sheet engineering. Circulation. 4 Jul. 2006; 114 (1 Suppl1): 187-93.

SUMMARY

Technical Problem

Although attempts to fabricate thick three-dimensional biological tissue by layering sheet-like tissue (e.g., cell sheets) are being carried out, sheet-like tissue is extremely thin and fragile and so required the expertise of a skilled operator to layer the sheets into a desired shape. In particular, it is difficult to layer sheet-like tissue on the inner wall of tubular tissue and so a new method for more easily layering sheet-like tissue without depending on the skill of an operator was needed. With respect to such a problem, it is the object of the present invention to provide a method for simply and stably fabricating tubular tissue. In addition, it is also the object to provide a tubular tissue preparation device and a tubular tissue preparation kit for implementing the method.

Solution to Problem

With respect to the above problem, as a result of extensive research carried out by the present inventors, it was found that by applying negative pressure to a tubular support the tubular support could be enlarged in a non-contact state and thereby the development of a tubular tissue preparation device, a tubular tissue preparation kit, and a tubular tissue preparation method that allows the simple and stable fabrication of tubular tissue without depending on the expertise of a skilled operator was achieved. Specifically, the present invention relates to the following.

[1] A tubular tissue preparation device comprising:
a chamber for accommodating a tubular support;
a first support for allowing the inside and outside of the chamber to communicate with each other and for securing the tubular support;
and a pressure increasing/decreasing means for controlling the pressure of an internal space of the chamber, wherein
the first support is used for securing a first opening of the tubular support, allowing a lumen of the tubular support to communicate with the outside of the chamber, and separating the lumen of the tubular support from the internal space of the chamber.

[2] The device according to [1] further comprising a second support for allowing the inside and outside of the chamber to communicate with each other and for securing the tubular support thereto, wherein the second support is used for securing a second opening of the tubular support, allowing the lumen of the tubular support to communicate with the outside of the chamber, and separating the lumen of the tubular support from the internal space of the chamber.

[3] The device according to [1] or [2] further comprising a fluid inlet/outlet provided to the chamber for allowing the inside and outside of the chamber to communicate with each other wherein the pressure increasing/decreasing means is connected to the fluid inlet/outlet.

[4] The device according to [3] wherein the pressure increasing/decreasing means is a syringe.

[5] The device according to [3] or [4] wherein a valve mechanism is provided between the pressure increasing/decreasing means and the fluid inlet/outlet.

[6] The device according to any one of [1] to [5] wherein the tubular support is provided to the chamber.

[7] The device according to any one of [1] to [6] wherein the tubular support is a biological tissue-derived tubular support.

[8] The device according to any one of [1] to [7] further comprising:

an arterial connection communicating with the inside and outside of the chamber and connected to a culture medium supply channel; and a vein connection communicating with the inside and outside of the chamber and connected to a culture medium discharge channel.

[9] A tubular tissue preparation kit comprising the device according to any one of [1] to [8] and a sheet-like tissue transfer device.

[10] The kit according to [9] wherein the sheet-like tissue transfer device has an expansion/contraction means.

[11] A tubular tissue preparation method involving the use of a tubular tissue preparation device comprising:

a chamber for accommodating a tubular support;

a first support for allowing the inside and outside of the chamber to communicate with each other and for securing the tubular support;

and a pressure increasing/decreasing means for controlling the pressure of an internal space of the chamber, wherein the method comprises the steps of:

(1) securing a first opening of the tubular support to the first support so that the lumen of the tubular support and the outside of the chamber are in communication, (2) separating the lumen of the tubular support from the internal space of the chamber, (3) expanding the tubular support by reducing the pressure of the internal space of the chamber with the pressure increasing/decreasing means, and (4) attaching the sheet-like tissue to an inner wall of the tubular support by inserting a sheet-like tissue transfer device supporting a sheet-like tissue through an external end opening of the first support.

[12] The method according to [11], wherein the tubular tissue preparation device further comprises a second support for allowing the inside and outside of the chamber to communicate with each other and for securing the tubular support, wherein the step (2) is a step of securing a second opening of the tubular support to the second support so that the lumen of the tubular support and the outside of the chamber are in communication.

[13] The method according to [11] or [12] further comprising, after the step (4), a step (5) of contracting the tubular support by increasing the pressure in the internal space of the chamber with the pressure increasing/decreasing means.

[14] The method according to any one of [11] to [13] wherein the sheet-like tissue transfer device has an expansion/contraction means.

[15] The method according to any one of [11] to [14] wherein the steps (3) and (4) are repeated an arbitrary number of times.

Advantageous Effects of Invention

According to the present invention, even if the tubular support has a complicated shape, sheet-like tissue can be easily and stably attached to and layered on the inner wall thereof. A thick tubular tissue can thereby be provided simply and with good reproducibility.

BRIEF DESCRIPTION OF DRAWINGS

FIGS. 2, 3A-3C, 4 and 5 illustrate the cross-sectional views of the same plane P.

DESCRIPTION OF EMBODIMENTS

The present invention will be described through the following embodiments of the invention. However, the following embodiments are not intended to limit the invention according to the claims, and not all combinations of the features described in the embodiments are essential for the solution to the problem to be solved by the invention.

Herein, "tubular tissue" refers to a structure obtained by attaching sheet-like tissue to a tubular support.

Herein, "tubular support" refers to a structure having a lumen structure, particularly a biological tissue-derived lumen structure. For the tubular support, for example, the intestinal tract (small intestine, large intestine, etc.), digestive tract such as esophagus and stomach, blood vessel, lymphatic duct, bile duct, ureter, bladder, urethra, trachea, uterus, oviduct and the like can be used. Conventionally, in most cases, such tubular supports were in a contracted state and when attempting to attach a sheet-like tissue to the inside thereof, the sheet-like tissue would fall off before reaching the desired position, and attachment was difficult. By applying the present invention, sheet-like tissue can be attached simply and stably even to a tubular support.

The tubular support may be harvested in a state in which arteries and veins are connected thereto so as to avoid necrosis of the sheet-like tissue to be attached thereto. Furthermore, the tubular support may be a tubular support that has been decellularized by a publicly-known method.

The tubular support used in the present invention has at least one opening. Herein, the term "opening (first opening and second opening)" is used to mean the opening and surrounding part thereof. The opening of the tubular support is secured to the support (first support or second support (discussed later)) which is provided in the tubular tissue preparation device of the present invention and is in communication with the space outside the tubular tissue preparation device chamber. The opening of the tubular support used in the present invention may be artificially formed using a scalpel, scissors, or the like.

Herein, "sheet-like tissue" refers to one or more layers of tissue shaped as a sheet comprising suitable cells. The sheet-like tissue may be harvested from biological tissue, may be obtained by culturing cells mixed with a hydrogel, or may be a cell sheet.

There are no particular restrictions on where the cells used to fabricate the sheet-like tissue are derived from. Examples include mammals such as humans, rats, mice, guinea pigs, marmosets, rabbits, dogs, cats, sheep, pigs, goats, monkeys, chimpanzees or immunodeficient versions thereof, birds, reptiles, amphibians, fish, and insects. Furthermore, the type and number of cells used to fabricate the sheet-like tissue and the ratio of cells included, can be selected and adjusted as appropriate according to the application thereof.

Herein, "cell sheet" refers to one or more layers of a cell group obtained by culturing cells on a cell culture substrate then peeling the cells thereof. The method for obtaining a cell sheet may encompass the following methods: a method involving culturing cells on a stimulus responsive culture substrate which is covered by a polymer, the molecular structure of which changes depending on a stimulus such as temperature, pH, or light, and changing the stimulus conditions such as temperature, pH, or light to change the stimulus responsive culture substrate surface such that the state of intercellular adhesion is maintained while separating the cells in a sheet shape from the stimulus responsive culture substrate; or a method involving culturing cells on a suitable culture substrate and physically peeling the cell sheet off the edge of the cell culture substrate using tweezers or the like. A preferred embodiment is a method involving the use, as the stimulus responsive culture substrate, of a temperature responsive culture substrate which has a surface covered by a polymer with a hydration force which changes in a temperature range of 0 to 80° C. For example, cell sheets can be easily obtained by using UpCell® which is commercially available from CellSeed Inc. (Tokyo, Japan).

An appropriate combination of the tubular support and sheet-like tissue used in the present invention can be selected according to the purpose, and no limitations are applied thereto. The cells contained in the sheet-like tissue can also be selected as appropriate according to the purpose.

1. Tubular Tissue Preparation Device

Figure 1:
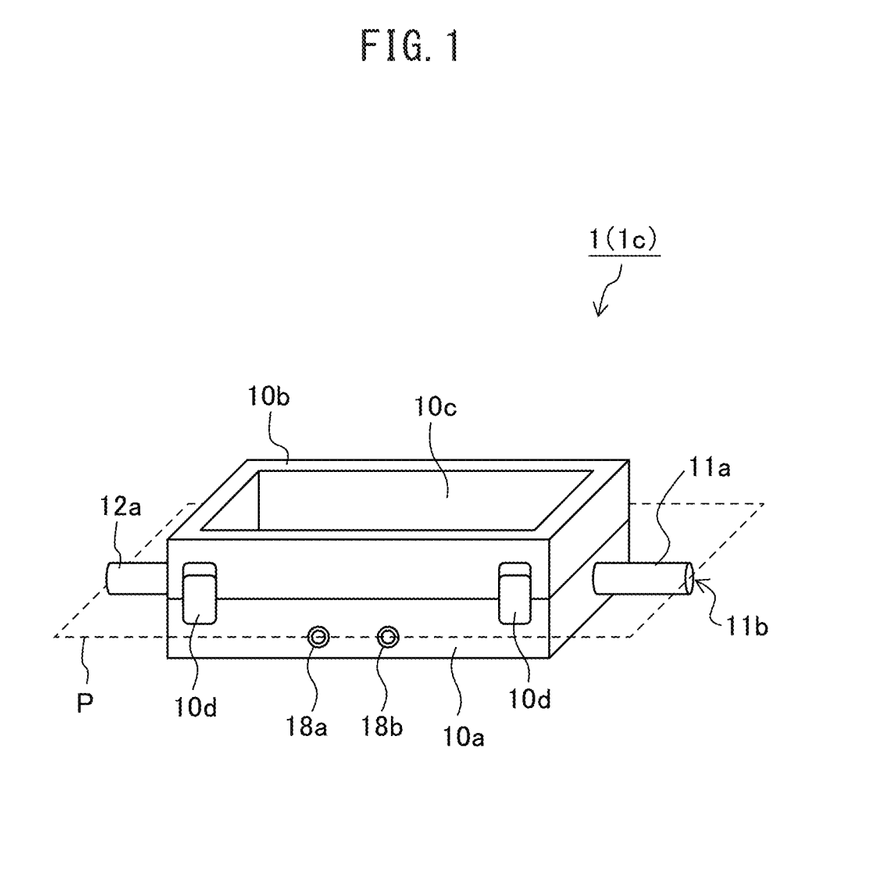
FIG. 1 is a perspective view of one embodiment of the tubular tissue preparation device. The schematic diagrams of the tubular tissue preparation device shown in the following

FIG. 1 shows a perspective view of the external appearance (FIG. 1 shows the external appearance of the tubular tissue preparation device 1c which will be discussed later) of the tubular tissue preparation device 1 according to one embodiment of the present invention. The diagrams of the tubular tissue preparation device 1 shown in FIGS. 2 to 5 illustrate the cross-sectional views of the same plane P of the tubular tissue preparation device 1 illustrated in FIG. 1.

1-1. First Embodiment

Figure 2:
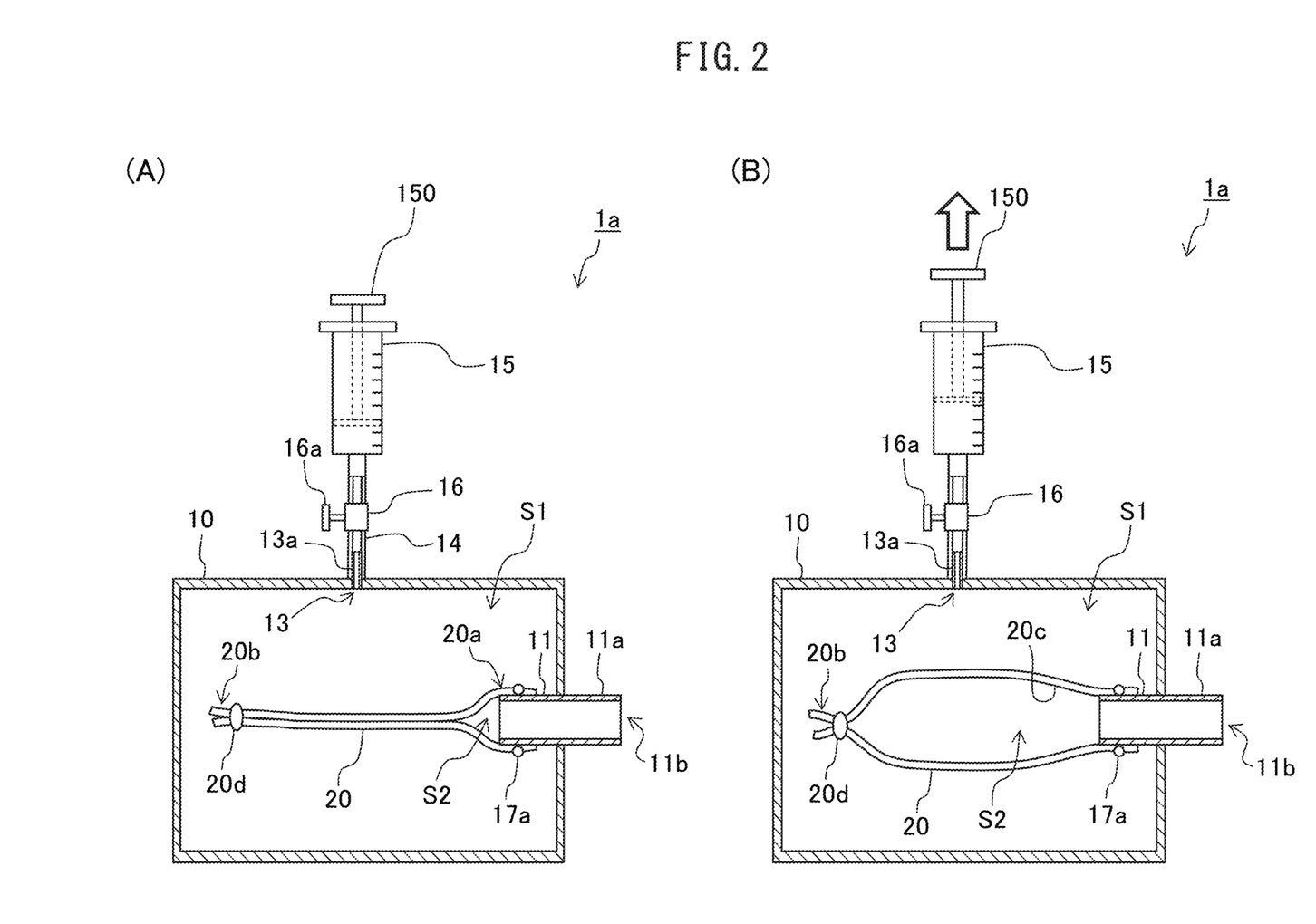

In one embodiment of the present invention illustrated in FIG. 2, the tubular tissue preparation device 1a comprises:
a chamber 10 for accommodating a tubular support 20;
a first support 11 for allowing the inside and outside of the chamber 10 to communicate with each other and for securing the tubular support 20;
and a pressure increasing/decreasing means 15 for controlling the pressure of an internal space S1 of the chamber 10, wherein
the first support 11 is used for securing a first opening 20a of the tubular support 20, allowing the lumen S2 of the tubular support 20 to communicates with the outside of the chamber, and separating the lumen S2 of the tubular support 20 from the internal space S of the chamber 10.

As shown in FIG. 1, the chamber 10 comprises a chamber body 10a and a chamber lid 10b. By combining the chamber body 10a and the chamber lid 10b, the space inside and outside the chamber 10 can be separated. The edges where the chamber body 10a and the chamber lid 10b are in tight contact with each other are each provided with a sealing member for ensuring a tight contact (e.g., an O-ring or packing). The chamber body 10a and the chamber lid 10b are fastened by a chamber fastener 10d. For the chamber fastener 10d, for example, a plurality of draw latches for fastening can be used. A window 10c, through which the inside of the chamber 10 can be seen, is provided in one part of the chamber lid 10b.

A first support 11 is provided in one part of the chamber 10 for allowing the inside and outside of the chamber 10 to communicate with each other and for securing the tubular support 20. Since the first support 11 allows the inside and outside of the chamber 10 to communicate with each other, it is possible to equalize the pressure in the tubular support 20 and the space outside the chamber 10. The first support 11 is provided so as to protrude to the inside of the chamber 10 so that the first opening 20a of the tubular support 20 can be secured. The first support 11 has a cylindrical shape and plays a role in allowing the space inside and outside the chamber 10 to communicate with each other. The shape of the first support is not limited to a cylindrical shape and may be a hollow prism (e.g., a triangular, square, or hexagonal prism). The diameter of the first support 11 can be appropriately changed according to the diameter of the tubular support 20 being used. The outer part (first external end part 11a of the first support) of the first support 11 of chamber 10 may have a shape that protrudes as shown in FIG. 2 but may be a shape with only a first external end opening 11b without protruding from the outer wall of chamber 10.

The first support 11 and the first opening 20a of the tubular support 20 are secured together by a first seal member 17a. The first seal member 17a may, for example, be a suture, and may also be a pipe clip made from silicone rubber, natural rubber, resin, metal, or the like. Further, the first seal member 17a may make use of a bioadhesive material such as fibrin gel, and any material may be applied provided the material has a function of bringing the first opening 20a into tight contact with the first support 11. A groove may be provided in a part of the first support 11 allowing the first seal member 17a to fit into the groove and thereby secure the first opening 20a of the tubular support 20 even tighter.

A pressure increasing/decreasing means 15 for controlling pressure of the internal space S1 of the chamber 10 is provided to the chamber 10. The pressure increasing/decreasing means 15, as shown in FIG. 2, is connected via a first channel 14 to the fluid inlet/outlet 13 that allows the inside and outside of the chamber 10 to communicate with each other. For the pressure increasing/decreasing means 15, a publicly-known means such as a syringe or a pump may be used. A syringe is preferable for the pressure increasing/decreasing means 15 since the mechanism is simple and fine adjustments for increasing or decreasing pressure can be made. The pressure increasing/decreasing means 15 may be provided on the chamber body 10a of the chamber 10 or may be provided on the chamber lid 10b.

In another embodiment, a valve mechanism 16 is further provided in the first channel 14 between the pressure increasing/decreasing means 15 and the fluid inlet/outlet 13. For the valve mechanism 16, a two-way stopcock or a clip, for example, may be used. By turning a cock 16a of the valve mechanism 16, the pressure of the internal space S1 of the chamber 10 which was increased or decreased by the pressure increasing/decreasing means 15 can be kept at a fixed level.

When using the tubular tissue preparation device 1a of the present embodiment, if the tubular support 20 has an opening (e.g., second opening 20b in FIG. 2(A)) other than the first opening 20a, it is necessary for the opening to be closed with an opening closure means 20d or the like. The lumen S2 of the tubular support 20 and the internal space S2 of the chamber 10 can be thereby separated. In this state, a reduction in pressure of the internal space S2 of the chamber 10 by the pressure increasing/decreasing means 15 will cause a pressure difference between the inside and outside of the tubular support 20 resulting in the tubular support 20 expanding. Accordingly, although conventionally it was difficult to attach a sheet-like tissue without damaging the tissue when attaching sheet-like tissue to the inside of a tubular support due to the tubular support shrinking and collapsing, sheet-like tissue can now be attached simply and securely.

1-2. Second Embodiment

Figure 3A:
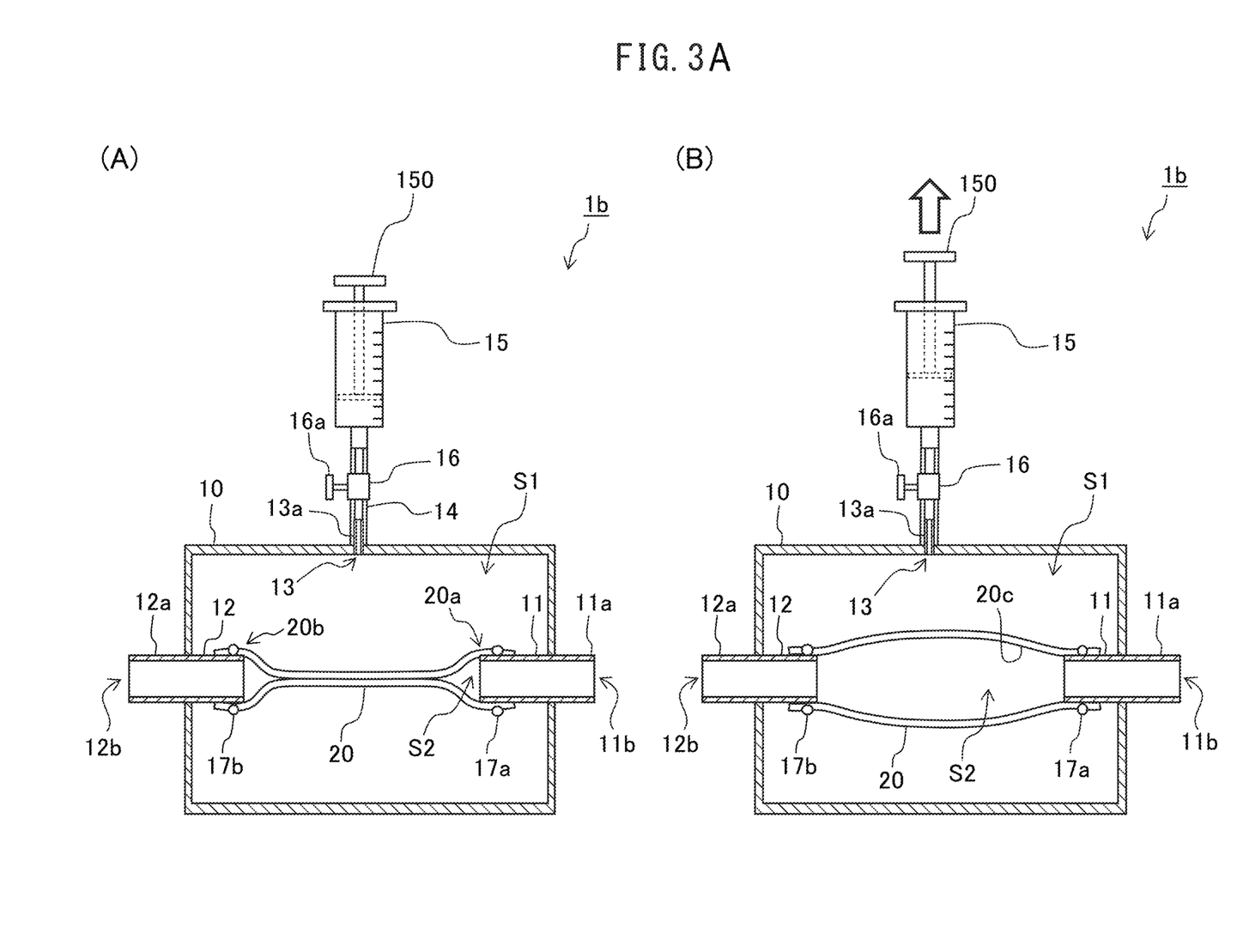
FIG. 3A is a schematic cross-section showing one embodiment of the tubular tissue preparation device.
Figure 3B:
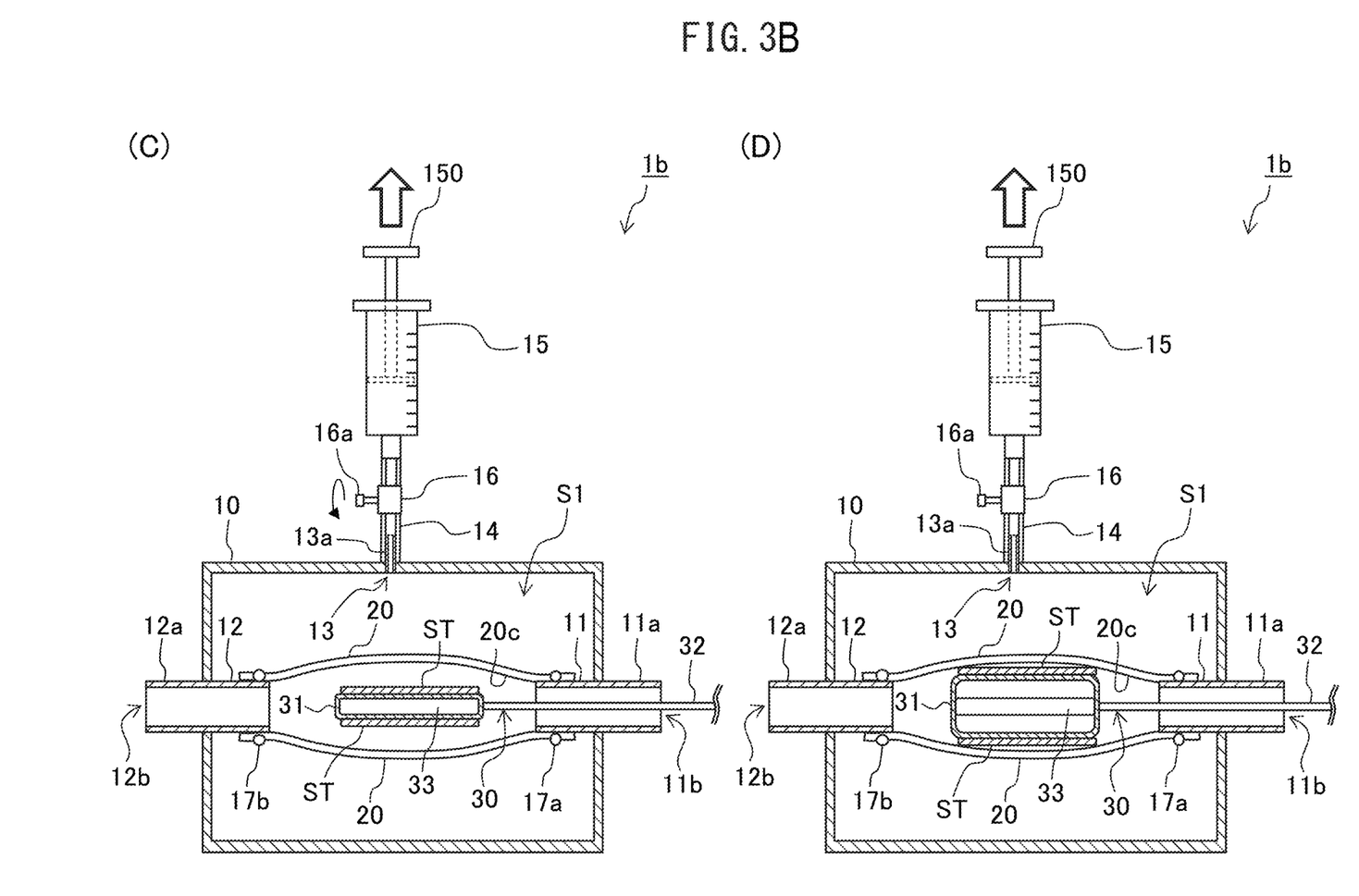
FIG. 3B is a schematic cross-section showing one embodiment of the tubular tissue preparation device.
Figure 3C:
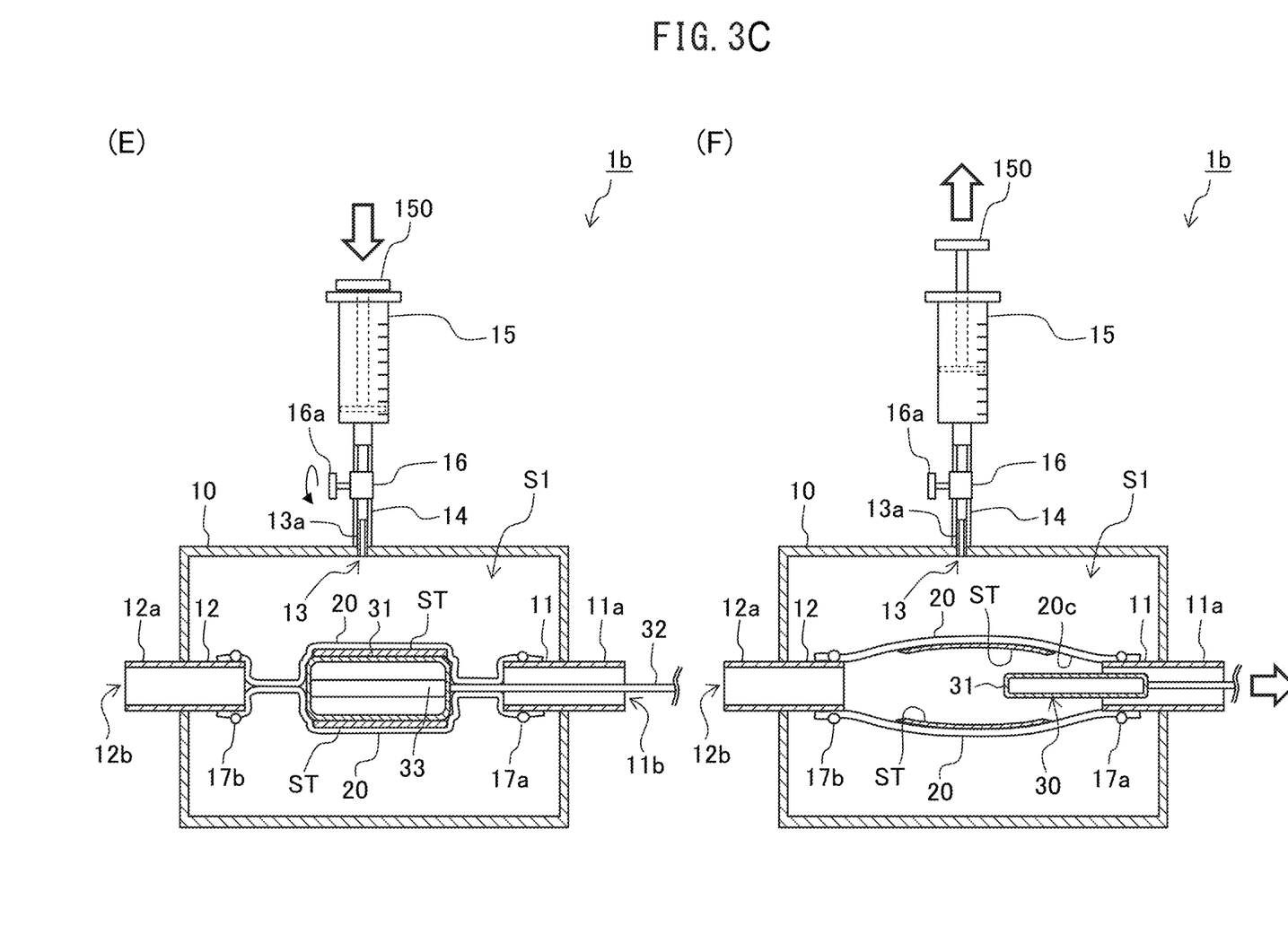
FIG. 3C is a schematic cross-section showing one embodiment of the tubular tissue preparation device.

In one embodiment of the present invention shown in FIG. 3A to FIG. 3C, the tubular tissue preparation device 1b, in addition to each of the members of the a second support 12 for allowing the inside and outside of the chamber 10 to communicate with each other and for securing the tubular support FIGS. 3A to 3C.

The second support 12 secures the second opening 20b of the tubular support 20, allows the lumen S2 of the tubular support 20 to communicate with the outside of the chamber 10, and separates the lumen S2 of the tubular support 20 from the internal space S1 of the chamber. Since the second support 12 allows the inside and outside of the chamber 10 to communicate with each other, it is possible to equalize the pressure in the tubular support 20 and the external space of the chamber 10. The second support 12 is provided so as to protrude to the inside of the chamber 10 so that the second opening 20b of the tubular support 20 can be secured. The second support 12 has a cylindrical shape and plays a role in allowing the inside space and outside space of the chamber 10 to communicate with each other. The shape of the second support 12 is not limited to a cylindrical shape and may be a hollow prism (e.g., a triangular, square, or hexagonal prism). The diameter of the second support 12 can be appropriately changed according to the diameter of the tubular support 20 being used. The outer part (second external end part 12a of the second support) of the second support 12 of chamber 10 may have a shape that protrudes as shown in FIG. 3 but may be a shape with only a second external end opening 12b without protruding from the outer wall of chamber 10.

The second support 12 and the second opening 20b of tubular support 20 are secured together by a second seal member 17b. The second seal member 17b may, for example, be a suture, and may also be a pipe clip made from silicone rubber, natural rubber, resin, metal, or the like. Further, the second seal member 17b may make use of a bioadhesive material such as fibrin gel and any material may be applied provided the material has a function of bringing the second opening 20b into tight contact with the second support 12. A groove may be provided in a part of the second support 12 allowing the second seal member 17b to fit into the groove and thereby secure the first opening 20a of the tubular support 20 even tighter.

The second support 12 may have the same diameter as the first support 11 or a different diameter. The first support 11 and the second support 12 are arranged so as face each other at both ends of the chamber 10. Thereby, the tubular support 20 can be evenly expanded (FIG. 3A (B)).

1-3. Third Embodiment

Figure 4:
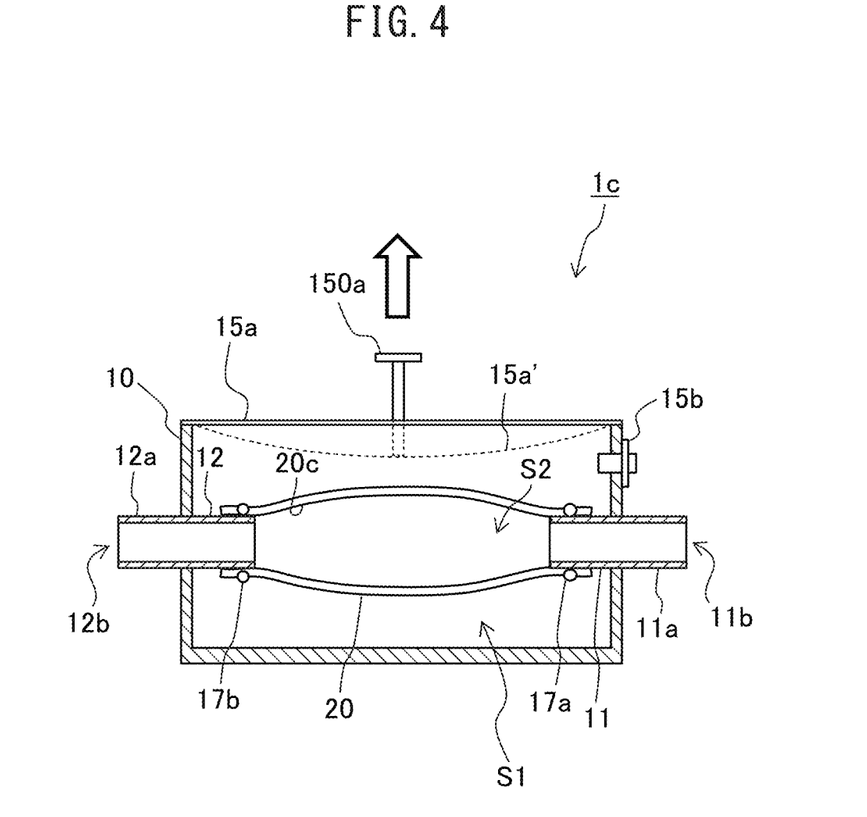
FIG. 4 is a schematic cross-section showing one embodiment of the tubular tissue preparation device.

In one embodiment of the present invention shown in FIG. 4, the tubular tissue preparation device 1c has an elastic member 15a in at least one part of the chamber 10 as the pressure increasing/decreasing means 15 of the tubular tissue preparation device 1a or the tubular tissue preparation device 1b. A check valve 15b is further provided in a part of the chamber 10. The elastic member 15a has a gripping part 150a for applying a force to the elastic member 15a. When the elastic member 15a is pushed (elastic member 15a' of FIG. 4), the volume of the internal space S1 of the chamber 10 decreases, and fluid present in the internal space S1 is discharged outside the chamber 10 via the check valve 15b. Thereafter, by pulling the gripping part 150a the elastic member 15a returns to the original shape or is deformed to have a more protruding shape. At this time, since the volume of the internal space S1 of the chamber 10 increases without fluid being resupplied thereto, the pressure within the internal space S1 decreases. As a result, a pressure difference between the inside and outside of the tubular support 20 is generated resulting in the tubular support 20 expanding. Accordingly, although conventionally it was difficult to attach a sheet-like tissue without damaging the tissue when attaching sheet-like tissue to the inside of a tubular support due to the tubular support shrinking and collapsing, sheet-like tissue can now be attached simply and securely.

1-4. Fourth Embodiment

Figure 5:
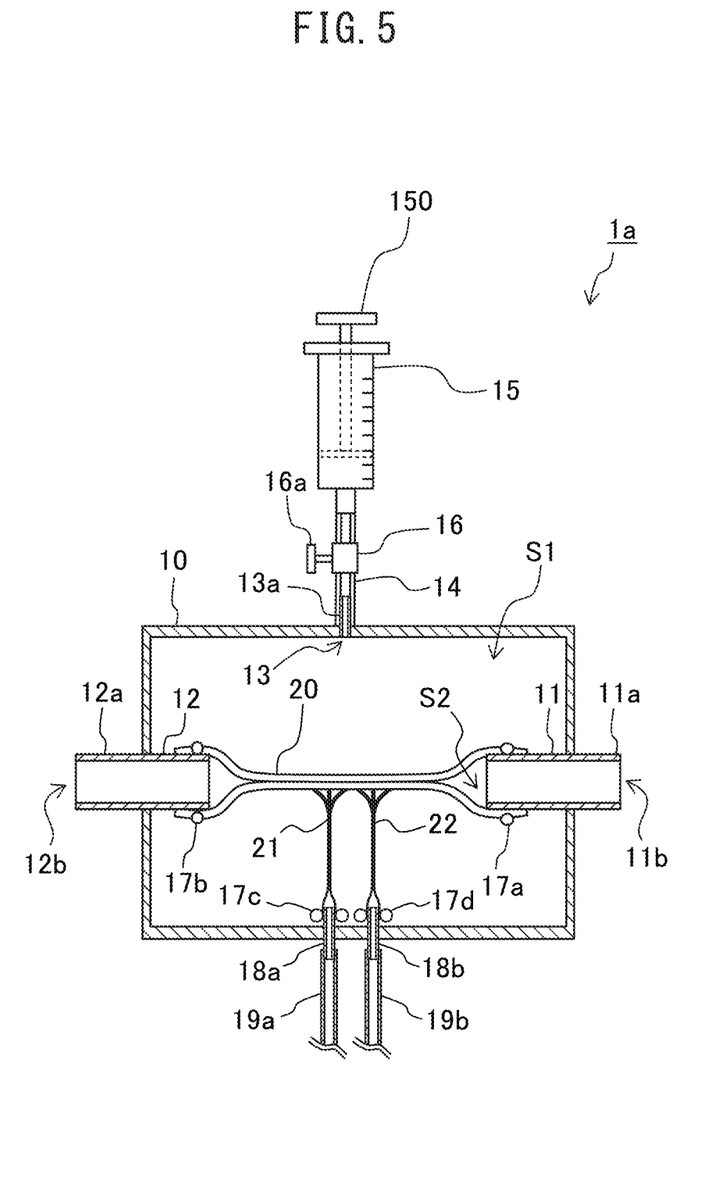
FIG. 5 is a schematic cross-section showing one embodiment of the tubular tissue preparation device.

In one embodiment of the present invention shown in FIG. 5, the tubular tissue preparation device 1d, in addition to each of the members of the tubular tissue preparation device 1a, the tubular tissue preparation device 1b or the tubular tissue preparation device 1c, further comprises in a part of the chamber 10:

an arterial connection 18a that communicates with the inside and outside of the chamber 10 and is connected to a culture medium supply channel 19a; and a vein connection 18b that communicates with the inside and outside of the chamber 10 and is connected to a culture medium discharge channel 19b.

When the tubular support 20 has an artery 21 and a vein 22, the artery 21 and the vein 22 may be respectively connected to the arterial connection 18a and the vein connection 18b.

The arterial connection 18a communicates with the culture medium supply channel 19a and is further connected to a culture medium supply means (not shown). Thereby, the culture medium contained in the culture medium supply means can be supplied to the tubular support 20, and even while the tubular tissue is being constructed, the sheet-like tissue that is to be attached can be prevented from becoming ischemic.

The vein connection 18b communicates with the culture medium discharge channel 19b and is further connected to a culture medium discharge layer (not shown). Thereby, culture medium consumed by the tubular support 20 supplied by the culture medium supply means can be efficiently discharged outside the chamber 10.

2. Tubular Tissue Preparation Kit

In one embodiment, the present invention provides a tubular tissue preparation kit comprising the aforementioned tubular tissue preparation device 1 (1a, 1b, 1c, and 1d) and a sheet-like tissue transfer device 30.

The sheet-like tissue transfer device 30 can have a function by which a sheet-like tissue is placed thereon and the sheet-like tissue ST is attached to a suitable position of the inner wall 20c of tubular support 20. For example, the device disclosed in Japanese Unexamined Patent Publication (Kokai) No. 2008-79783 or WO2017/043600 can be used. Put simply, the sheet-like tissue transfer device 30, as shown in FIG. 3B (C), has a fluid supply tube 32, a tube-like part 33 provided at the tip thereof, and an expansion/contraction means 31 provided so as to be expandable and contractible on the outer surface of the tube-like part 33. A sheet-like tissue ST is wound onto the expansion/contraction means 31. After expansion by the tubular tissue preparation device 1 (1a, 1b, 1c, and 1d), a sheet-like tissue transfer device 30 with a sheet-like tissue ST supported thereby is inserted through the first external end opening 11b of the first support 11. Thereafter, fluid is sent to the expansion/contraction means 31 via the fluid supply tube 32 and the expansion/contraction means 31 is expanded. Thereby, the sheet-like tissue ST can be brought into tight contact with the inner wall 20c of the tubular support 20 and the sheet-like tissue ST can be attached to the inner wall 20c of the tubular support 20.

The sheet-like tissue transfer device 30 may have any shape provided at least a sheet-like tissue can be placed thereon and it can pass through the first external end opening 11b of the first support 11. In order to be able to simply and uniformly attach the sheet-like tissue ST to the inner wall 20c of the tubular support 20, it is preferable to have an expansion/contraction means 31. For the expansion/contraction means, a balloon may be used, for example.

3. Tubular Tissue Preparation Method

The present invention provides a tubular tissue preparation method that involves the use of the aforementioned tubular tissue preparation device 1 (1a, 1b, 1c, or 1d), and a sheet-like tissue transfer device 30. Note that the tubular tissue preparation device 1 (1a, 1b, 1c, or 1d) and the sheet-like tissue transfer device 30 are the same as those described above.

In one embodiment, the tubular tissue preparation method involves the use of a tubular tissue preparation device 1a comprising:

a chamber 10 for accommodating a tubular support 20;

a first support 11 for allowing the inside and outside of the chamber 10 to communicate with each other and for securing the tubular support 20; and a pressure increasing/decreasing means 15 for controlling the pressure of the space S1 within the chamber 10, wherein the method comprises the steps of (1) securing a first opening 20a of the tubular support 20 to the first support 11 so that the lumen S2 of the tubular support 20 and the outside of the chamber 10 are in communication, (2) separating the lumen S2 of the tubular support 20 from the internal space S1 of the chamber 10, (3) expanding the tubular support 20 by reducing the pressure of the internal space S1 of the chamber 10 with the pressure increasing/decreasing means 15, and (4) attaching the sheet-like tissue ST to the inner wall 20c of the tubular support 20 by inserting a sheet-like tissue transfer device 30 supporting a sheet-like tissue ST through the first external end opening 11b of the first support 11.

When using the tubular tissue preparation device 1a, if the tubular support 20 has an opening (e.g., second opening 20b in FIG. 2(A)) other than the first opening 20a, it is necessary for the opening to be closed with an opening closure means 20d or the like. Thereby, the lumen S2 of the tubular support 20 can be separated from the internal space S2 of the chamber 10 (step (2)).

In another embodiment, the tubular tissue preparation method may involve the use of a tubular tissue preparation device 1b further comprising a second support 12 for allowing the inside and outside of the chamber 10 to communicate with each other and for securing the tubular support 20. In such cases, by implementing, as the step (2), a step of securing the second opening 20b of the tubular support 20 to the second support 12 such that the lumen S2 of the tubular support 20 communicates with the outside of the chamber 10, the lumen S2 of the tubular support 20 can be separated from the internal space S2 of the chamber 10.

In another embodiment, after the step (4), a further step (5) of contracting the tubular support 20 by increasing the pressure in the internal space Si of the chamber 10 with the pressure increasing/decreasing means 15 can be implemented (FIG. 3C).

As shown in FIG. 3C (E), by increasing pressure in the internal space S1 of the chamber 10 by the pressure increasing/decreasing means 15, the inner wall 20c of the tubular support 20 and the sheet-like tissue ST can be brought into tighter contact. Thereby, engrafting of the attached sheet-like tissue ST onto the tubular support 20 can be promoted.

In another embodiment, by repeating the steps (3) and (4) an arbitrary number of times, the sheet-like tissue can be layered an arbitrary number of times. Thereby, a thick tubular tissue can be provided simply and stably.

The degree by which the pressure is decreased and/or increased by the pressure increasing/decreasing means (pressure increasing/decreasing means 15 and elastic member 15a) of the tubular tissue preparation device 1 (1a, 1b, 1c, or 1d) of the present invention can be appropriately adjusted depending on the properties of the tubular support 20 being used and the degree of expansion/contraction of the tubular support 20 can be appropriately adjusted while being observed.

EXAMPLES

The present invention will be further described in detail based on the following examples but is not in any way limited thereby. Note that experiments in the examples were conducted in line with the Detailed Regulations for Enforcement of Safety Management Rules for Biological Experiments of Waseda University and Tokyo Women's Medical University after approval by the Animal Experiment Ethics Committee of both universities.

<Animals, Cells, and Reagents Used>

The following animals, cells, and reagents, were used in the present example.

Rat (LEW/CrlCrlj)

Cardiomyocytes (Human iPS cell strain 201B7)

Temperature-responsive culture dish (UpCell®) (CellSeed Inc.)

FBS (Japan Bio Serum, S1650-500)

DMEM (SIGMA, D6429)

Penicillin-streptomycin solution (Life Technologies, 15140-122)

4% paraformaldehyde fixative (Muto Pure Chemicals Co., Ltd., 3311-1)

Anti-rat cardiac troponin T (cTNT) antibodies (Thermo Fisher Scientific, MS-295-P1)

Secondary staining antibody (Thermo Fisher Scientific, A11019)

Hoechst (Dojindo, Hoechst3325)

<Method for Collecting Tubular Support (Small Intestine)>

The tubular support (small intestine) used in the example was harvested as described below.

A rat anesthetized with a 3% concentration of isoflurane was subjected to a midline incision in the abdomen to expose the ileum. The ileum and the ileum artery and vein were separated using scissors and were separated by cutting 5 cm from the ileal orifice side toward the ileum side.

<Method for Preparing Cardiomyocyte Sheet>

The cardiomyocytes were prepared by the method according to Matsuura et al. (Katsuura M. et al., Creation of human cardiac cell sheets using pluripotent stem cells, Biochemical and Biophysical Research Communications, 425, 2012). Specifically, human iPS cells were induced to differentiate into cardiomyocytes in a rotary bioreactor and collected. When inducing differentiation, StemPro34 culture medium in which 50 μg/ml of ascorbic acid (Sigma-Aldrich), 2 mM of L-glutamine, and 400 μM of 1-thioglycerol (Sigma-Aldrich) were mixed was used as the basic medium, and the following growth factors were added thereto.

(1) Day 0 to 1: 0.5 ng/mL BMP4 (R&D systems, Minneapolis, Minn.);

(2) Day 1 to 4: 10 ng/ml BMP4, 5 ng/ml bFGF, 3 ng/ml activin A (R&D systems);

(3) Day 4 to 6: 4 μM IWR-1 (Wako);

(4) Day 6 to 16: 5 ng/ml VEGF, 10 ng/ml bFGF.

The culture medium was exchanged on days 1, 4, 6, 8, 10, 12, and 14.

Cells collected on day 16 from the bioreactor were inoculated at a concentration of $1.0 \times 10^7$ cells/10 cm dish. The culture medium used at this time was DMEM containing 10% FBS and 1% penicillin/streptomycin. From the day after inoculation, puromycin was mixed therein to a concentration of 100 ng/ml and the mixture was cultured in an incubator at 37° C. under 5% $CO_2$ and saturated water vapor. The culture medium was exchanged on days 1, 3, 5, 7, 10, and 12, and on day 14 a Trypsin-EDTA solution was used to collect the cells. The collected cells and human dermal fibroblasts were each inoculated on a 35 mm temperature responsive culture dish (UpCell®, CellSeed Inc.), at a concentration of 1,000,000 cells/culture dish and were cultured in DMEM containing 10% FBS and 1% penicillin/streptomycin in an incubator at 37° C. under 5% $CO_2$ and saturated water vapor. Thereafter, a cell sheet was collected while maintaining the temperature at 20° C.

<Hematoxylin and Eosin (H&E) Staining, Immunostaining>

The collected tissue was fixed with paraffin, sliced to a thickness of 5 μm, and the morphology of the layered cells was evaluated by staining with H&E staining or immunostaining.

Example 1

<Method for Layering Cardiomyocyte Sheet onto Small Intestine Inner Wall>

The openings at both ends of the tubular small intestine were connected to silicone tubes (corresponding to first support 11 and second support 12 in FIG. 6) in communication with the outside of the chamber. Thereby, the lumen of the small intestine is constantly maintained at atmospheric pressure. The lid of the sealed chamber has a portion that is open to the atmosphere via a silicone tube and air was drawn into the chamber from this portion. Thereby, the pressure inside the chamber was reduced so that a pressure difference was generated with the lumen of the small intestine that was maintained at atmospheric pressure. The pressure inside the chamber was reduced until the small intestine was expanded by the pressure difference generated at this time. When the small intestine was in a completely expanded state the portion open to the atmosphere was blocked and the internal pressure was maintained by sealing the space within the chamber. Thereby, it was possible to maintain the small intestine in an expanded state and insert the sheet-like tissue transfer device into the expanded small intestine and attach cell sheets onto the inner wall of the small intestine (FIG. 6).

Example 2

Figure 6:
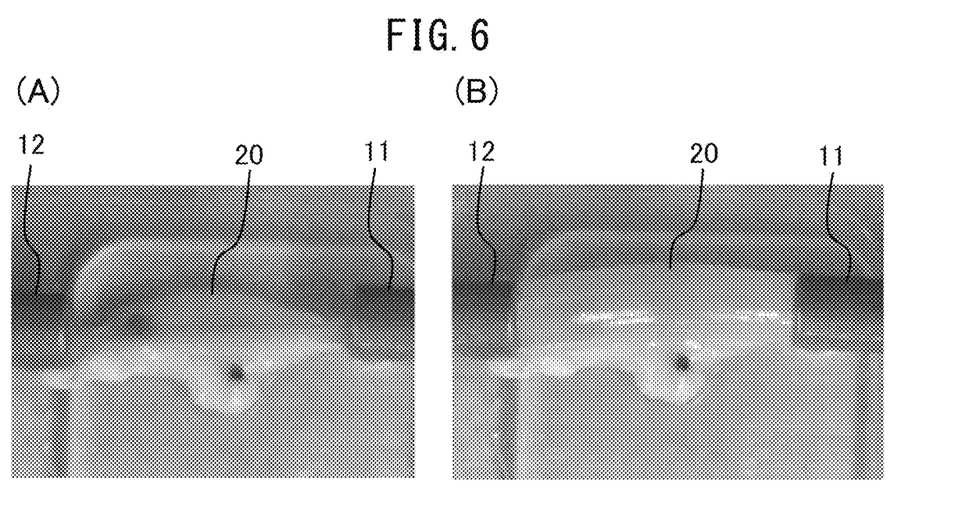
FIG. 6 shows pictures of the small intestine before and after decompression using the tubular tissue preparation device of the present invention. (A) is the small intestine before decompression and (B) is the small intestine after decompression.
Figure 7:
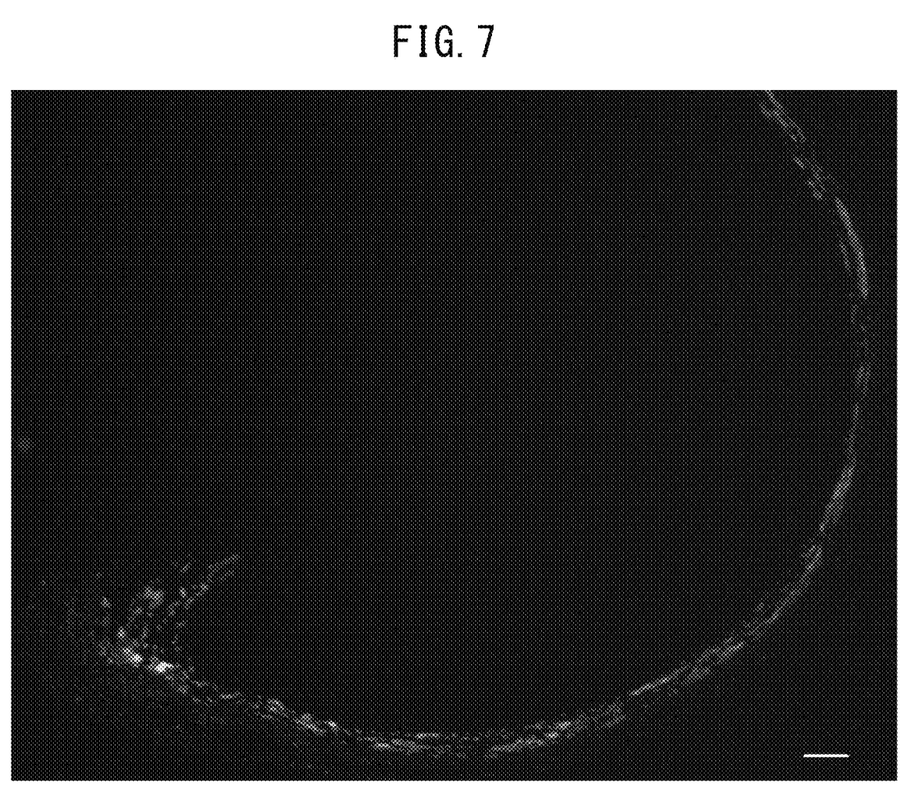
FIG. 7 shows an image of a tubular tissue section fabricated using the tubular tissue preparation device of the present invention. A stained image in which the cell nuclei (blue, Hoechst) and cardiac troponin T (green, cTnT) of the tubular tissue is shown. The scale bar shows 100 µm.
Figure 8:
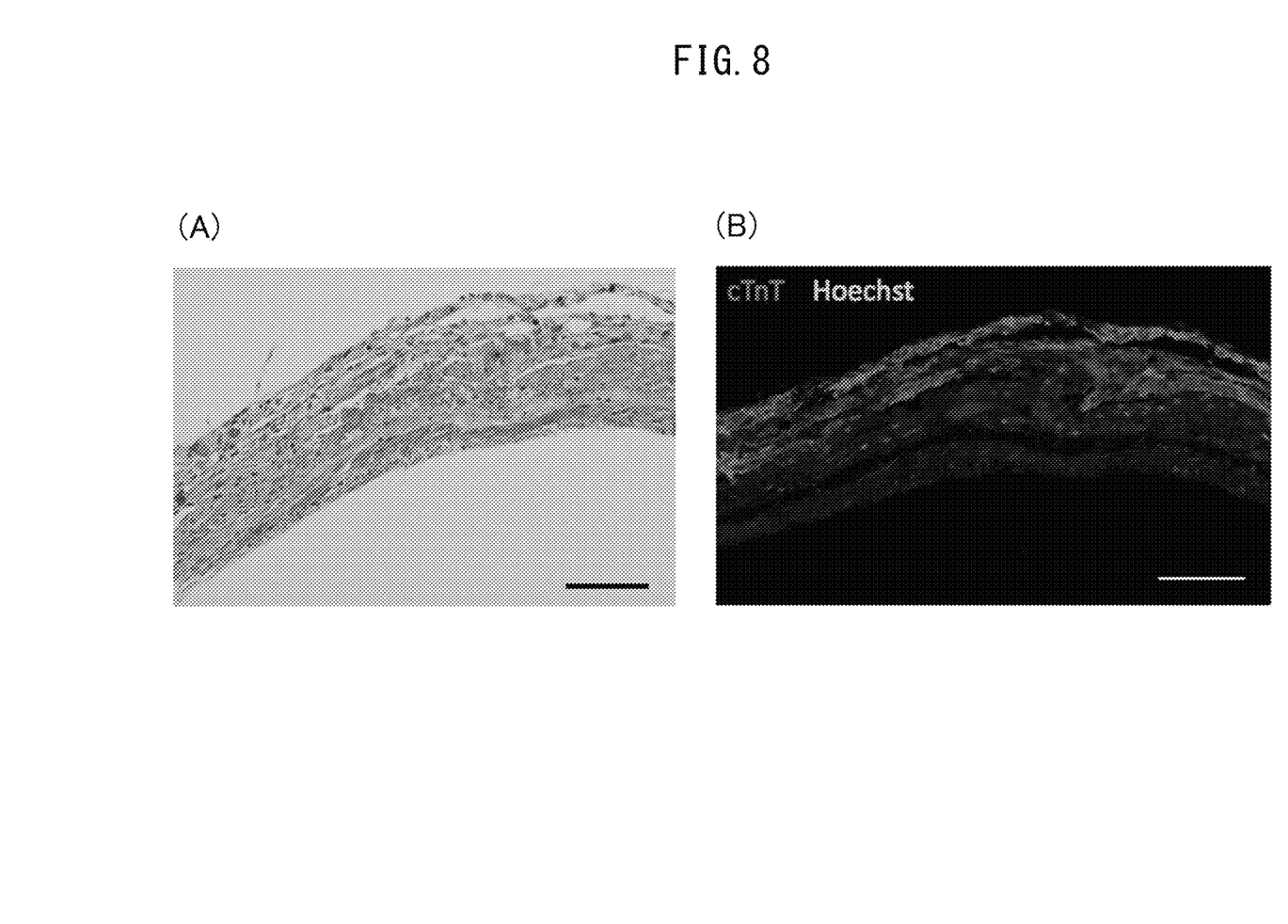
FIG. 8 shows an image (enlarged view) of a tubular tissue section fabricated using the tubular tissue preparation device of the present invention. (A) is an H&E stained image, (B) is a stained image in which the cell nuclei (blue, Hoechst) and cardiac troponin T (green, cTnT) are shown. The scale bar shows 100 µm.

Results of Reducing Pressure and Layering Cardiomyocyte Sheet onto Small Intestine Inner Wall When the small intestine was expanded by pressure reduction with the tubular tissue preparation device used in the present invention, the small intestine expanded due to the pressure difference (FIG. 6). The sheet-like tissue transfer device was inserted into the expanded small intestine, a cardiomyocyte sheet was layered onto the inner wall, and it could be confirmed that the cell sheet was attached to the small intestine inner wall (FIG. 7). Furthermore, it could be confirmed that the attached cardiomyocyte sheet was layered according to the shape of the small intestine (FIG. 8). This can be considered to be a result of the cardiomyocyte sheet being pressure-bonded by layering using the tubular tissue preparation device of the present invention. Furthermore, it is possible to adjust the degree of pressure bonding of the cardiomyocyte sheet to the small intestine by increasing the pressure using the tubular tissue preparation device of the present invention.

REFERENCE SIGNS LIST

1, 1a, 1b, 1c, 1d: tubular tissue preparation device; 10: chamber; 10a: chamber body; 10b: chamber lid; 10c: window; 10d: chamber fastener; 11: first support; 11a: first external end part; 11b: first external end opening; 12: second support; 12a: second external end part; 12b: second external end opening; 13: fluid inlet/outlet; 13a: connector; 14: first channel; 15: pressure increasing/decreasing means; 150: piston; 15a, 15a': elastic member; 150a: gripping part; 15b: check valve; 16: valve mechanism; 16a: cock; 17a: first seal member; 17b: second seal member; 17c: third seal member; 17d: fourth seal member; 18a: arterial connection; 18b: vein connection; 19a: culture medium supply channel; 19b: culture medium discharge channel; 20: tubular support; 20a: first opening; 20b: second opening; 20c: inner wall; 20d: opening closure means; 21: artery; 22: vein; 30: sheet-like tissue transfer device; 31: expansion/contraction means; 32: fluid supply tube; 33: tube-like part; S1: inner space; S2: lumen; ST: sheet-like tissue; P: same plane

The invention claimed is:

1. A tubular tissue preparation device comprising:
a chamber for accommodating a tubular support;
a first support for allowing the inside and outside of the chamber to communicate with each other and for securing the tubular support; and
a pressure increasing/decreasing means for controlling the pressure of the internal space of the chamber, wherein
the first support is used for securing a first opening of the tubular support, allowing a lumen of the tubular support to communicate with the outside of the chamber, and separating the lumen of the tubular support from the internal space of the chamber.

2. The device according to claim 1 further comprising a second support for allowing the inside and outside of the chamber to communicate with each other and for securing the tubular support, wherein
the second support is used for securing a second opening of the tubular support, allowing the lumen of the tubular support to communicate with the outside of the chamber, and separating the lumen of the tubular support from the internal space of the chamber.

3. The device according to claim 1 further comprising a fluid inlet/outlet provided to the chamber for allowing the inside and outside of the chamber to communicate with each other, wherein
the pressure increasing/decreasing means is connected to the fluid inlet/outlet.

4. The device according to claim 3 wherein the pressure increasing/decreasing means is a syringe.

5. The device according to claim 3 wherein a valve mechanism is provided between the pressure increasing/decreasing means and the fluid inlet/outlet.

6. The device according to claim 1 wherein the tubular support is provided to the chamber.

7. The device according to claim 1 wherein the tubular support is a biological tissue-derived tubular support.

8. The device according to claim 1 further comprising:
an arterial connection communicating with the inside and outside of the chamber and connected to a culture medium supply channel; and
a vein connection communicating with the inside and outside of the chamber and connected to a culture medium discharge channel.

9. A tubular tissue preparation kit comprising the device according to claim 1 and a sheet-like tissue transfer device.

10. The kit according to claim 9 wherein the sheet-like tissue transfer device has an expansion/contraction means.

11. A tubular tissue preparation method involving the use of a tubular tissue preparation device comprising:
a chamber for accommodating a tubular support;
a first support for allowing the inside and outside of the chamber to communicate with each other and for securing the tubular support;
and a pressure increasing/decreasing means for controlling the pressure of an internal space of the chamber, wherein the method comprises the steps of:
(1) securing a first opening of the tubular support to the first support so that the lumen of the tubular support and the outside of the chamber are in communication,
(2) separating the lumen of the tubular support from the internal space of the chamber,
(3) expanding the tubular support by reducing the pressure of the internal space of the chamber with the pressure increasing/decreasing means, and
(4) attaching the sheet-like tissue to an inner wall of the tubular support by inserting a sheet-like tissue transfer device supporting a sheet-like tissue through an external end opening of the first support.

12. The method according to claim 11, wherein the tubular tissue preparation device further comprises a second support for allowing the inside and outside of the chamber to communicate with each other and for securing the tubular support, wherein
the step (2) is a step of securing a second opening of the tubular support to the second support so that the lumen of the tubular support and the outside of the chamber are in communication.

13. The method according to claim 11 further comprising, after the step (4),
a step (5) for contracting the tubular support by increasing the pressure in the internal space of the chamber with the pressure increasing/decreasing means.

14. The method according to claims 11 wherein the sheet-like tissue transfer device has an expansion/contraction means.

15. The method according to claims 11 wherein the steps (3) and (4) are repeated an arbitrary number of times.

* * * * *